United States Patent [19]

Fabry et al.

[11] Patent Number: 4,956,116
[45] Date of Patent: Sep. 11, 1990

[54] SURFACE-ACTIVE, SATURATED SULFOPHOSPHORIC ACID-(PARTIAL)-ALKYL ESTERS

[75] Inventors: Bernd Fabry, Korschenbroich; Hans-Herbert Friese, Monheim; Friedrich Pieper, Langenfeld; Guenter Uphues, Monheim, all of Fed. Rep. of Germany

[73] Assignee: Henkel Kommanditgesellschaft auf Aktien, Duesseldorf, Fed. Rep. of Germany

[21] Appl. No.: 304,398

[22] Filed: Jan. 30, 1989

[30] Foreign Application Priority Data

Apr. 16, 1988 [DE] Fed. Rep. of Germany ....... 3812718

[51] Int. Cl.$^5$ ................. C11D 3/06; C11D 3/065; C11D 7/16; C11D 11/04
[52] U.S. Cl. ................. 252/174.16; 252/135; 252/DIG. 17; 558/70; 558/87
[58] Field of Search ........... 252/174.16, 135, 549, 252/DIG. 17, 551; 558/45, 70

[56] References Cited

U.S. PATENT DOCUMENTS

| 2,212,521 | 8/1940 | Harris | 252/551 |
| 2,336,230 | 12/1943 | Dickey et al. | 558/45 |
| 2,862,019 | 11/1958 | Schrader | 558/45 |
| 3,338,948 | 8/1967 | Hieronymons et al. | 252/549 |
| 3,346,505 | 10/1967 | Blakeway et al. | 252/551 |
| 3,484,474 | 12/1969 | Krause | 252/551 |
| 3,828,084 | 8/1974 | Kaplan et al. | 252/DIG. 17 |
| 4,390,465 | 6/1983 | Spekman, Jr. | 252/DIG. 17 |
| 4,707,292 | 11/1987 | Sano et al. | 252/DIG. 17 |
| 4,830,764 | 5/1989 | Wiedemann | 252/DIG. 17 |

OTHER PUBLICATIONS

"Soap, Cosmetic & Chemical Specialities" (1986) vol. 7, p. 26–Phosphate Esters, O'Lenick et al. (SCSS).
J. Am. Oil Chem. Soc. 41, 205 (1964); J. Am. Oil Chem. Soc. 64, 1038 (1987); Soap, Cosm, Spec. 7, 26 (1986).

Primary Examiner—Paul Lieberman
Assistant Examiner—A. Beadles-Hay
Attorney, Agent, or Firm—Ernest G. Szoke; Wayne C. Jaeschke; Real J. Grandmaison

[57] ABSTRACT

A process for preparing surface-active, saturated sulfophosphoric acid-(partial)-alkyl esters and their alkali metal, alkaline earth, ammonium and/or amine salts by the sulfonation of saturated phosphoric acid-(partial)-alkyl esters and then hydrolysis of the sulfonated phosphoric acid esters formed.

11 Claims, No Drawings

SURFACE-ACTIVE, SATURATED SULFOPHOSPHORIC ACID-(PARTIAL)-ALKYL ESTERS

BACKGROUND OF THE INVENTION

1. Field of the Invention:

This invention relates to a process for the manufacture of surface-active saturated sulfophosphoric acid-(partial)-alkyl esters and their alkali metal, alkaline earth, ammonium and/or amine salts by the sulfonation of saturated phosphoric acid-(partial)-alkyl esters and the hydrolysis of the sulfonated phosphoric acid esters formed.

2. Discussion of Related Art:

While the use of phosphates and phosphonates as builders in detergent compositions is widespread, phosphoric compounds have previously been used as surfactants only to a lesser degree.

The synthesis of surfactants containing phosphorus by the reaction of saturated α-bromo-fatty acid esters with triethylphosphite has been described more than 20 years ago by Maurer et al. in J. Am. Oil Chem. Soc. 41, 205 (1964). However the o-phosphono-fatty acid esters only have average surface-active properties. Recently, the manufacture of alkyl phosphinates by the reaction of alpha-olefins with phosphorous or hypophosphorous acids has been disclosed (C. Herranz in J. Am. Oil Chem. Soc. 64, 1038 (1987). These substances also only have moderate washing and foaming properties.

Compared with the surfactants described by Maurer and Herranz, in which phosphorus is directly linked with a carbon chain, phosphoric acid esters with P-O-C-bonds have clearly improved surfactant properties. It is, for example, known that alkyl phosphates can be used as wetting agents, antistatic agents, emulsifying agents and in detergents and cleaning agents (A. J. Olenick, W. C. Smith in Soap, Cosm. Chem. Spec. 7, 26 (1986)). However these substances have only a slight foaming capacity, they are less resistant to hard water, and some are poorly soluble in water.

From Acta Polym. 38, 5 (1987) the use of alkyl phosphates, manufactured by the reaction of alcohols or alcohol polyoxy alkyl ethers with $POCl_3$ as antistatic agents for synthetic fibers is also known.

An object of this invention is to improve the surface-active properties, the water solubility, and particularly the resistance to hard water of long-chain alkyl phosphates.

DESCRIPTION OF THE INVENTION

Other than in the operating examples, or where otherwise indicated, all numbers expressing quantities of ingredients or reaction conditions used herein are to be understood as modified in all instances by the term "about".

The invention is based upon the surprising discovery that saturated phosphoric acid-(partial)-alkyl esters containing sulfonate groups are distinguished by clearly improved surfactant properties, a better water solubility and an improved resistance to hard water.

An embodiment of this invention is accordingly a process for the manufacture of surface-active, saturated sulfophosphoric acid-(partial)-alkyl esters and their alkali metal, alkaline earth, ammonium and/or amine salts, comprising reacting saturated alkyl, saturated alkyl/saturated alkyl polyoxy alkyl, and/or saturated alkyl polyoxy alkyl phosphoric acid esters having an iodine number between 0 and less than 10, which correspond to general formula I

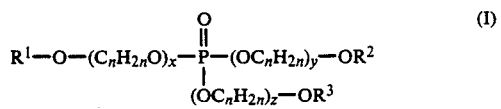

in which $R^1$ represents an alkyl group with 8 to 22 carbon atoms or a fatty alkyl group consisting predominatly of octyl, decyl, lauryl, myristyl, cetyl, stearyl and/or behenyl groups, the radicals $R^2$ and $R^3$ are the same or different and represent hydrogen, an alkyl group with 8 to 22 carbon atoms or a fatty alkyl group consisting predominatly of octyl, decyl, lauryl, myristyl, cetyl, stearyl and/or behenyl groups, n represents a number from 2 to 4, the subscripts x, y and z are the same or different and represent a number from 0 to 30, with a sulfonating agent; and hydrolyzing the reaction products with an aqueous solution of 1 to 1.5 mol. of alkali metal hydroxide, alkaline earth hydroxide, ammonium hydroxide, amine, or with 1 to 1.5 mol of anhydrous amine per mole of combined $SO_3$.

Saturated sulfophosphoric acid-(partial)-alkyl esters with particularly favorable surface active properties are obtained when for the sulfonation, saturated phosphoric acid-(partial)-alkyl esters of general formula I are used in which the radical $R^1$ represents an alkyl group with 12 to 18 carbon atoms or a fatty alkyl group consisting predominatly of lauryl, myristyl, cetyl and/or stearyl groups, the radicals $R^2$ and $R^3$ are the same or different and represent hydrogen, an alkyl group with 12 to 18 carbon atoms or a fatty alkyl group consisting predominatly of lauryl, myristyl, cetyl and/or stearyl groups, n is a number from 2 to 3, and the subscripts x, y, z are the same or different and represent a number from 0 to 10.

Saturated phosphoric acid-(partial)-alkyl esters of general formula I are preferably sulfonated at a temperature between 20° and 120° C., and particularly preferably at a temperature between 60° and 100° C., preferably with sulfuric acid, oleum, chlorosulfonic acid or gaseous mixtures containing $SO_3$. Gaseous mixtures of $SO_3$ and air or inert gases, e.g. nitrogen, in which the $SO_3$ content is between 1 and 10 percent by volume, are particularly preferred as sulfonating agents. The molar ratio of the ester equivalents contained in the educt (phosphoric acid ester): $SO_3$ is preferably between 100:5 and 100:180, and particularly preferably between 100:10 and 100:160.

The sulfonation may be carried out continuously or discontinuously in a usual reactor suitable and customary for the sulfating of fatty alcohols or for the sulfonation of fatty acid esters, alkylbenzenes or olefins, preferably of the "fall film" reactor type, (see, for example, Kirk-Othmer: Encyclopedia of Chemical Technology 22, 28 ff (1983)).

After the sulfonation is complete, it has proved particularly desirable in many cases to subject the reaction mixture to an aging process. To this end, the reaction mixture is left to stand or agitated for about 0 to 240 minutes, and particularly preferably for 1 to 30 minutes, preferably at 10° to 120° C., and particularly preferably at 60° to 100° C. The reaction mixture is then hydrolyzed with an aqueous solution of alkali metal hydroxide, alkaline earth hydroxide, ammonium hydroxide, amine or with anhydrous amine, in which either the reaction mixture is added to the aqueous hydroxide/a- mine solution or the anhydrous amine, or the aqueous hydroxide/amine solution or the anhydrous amine is added to the reaction mixture. Preferably, the aged reaction mixture is introduced to an aqueous solution of alkali metal hydroxide, alkaline earth hydroxide, ammonium hydroxide and/or amine, whereby per mole of combined sulfur trioxide 1 to 1.5 mol. of hydroxide and/or amine is used. The hydroxide and/or amine hydrolyzes and neutralizes the sulfonation product; excess hydroxide and/or amine being necessary to neutralize the gaseous SO₃ dissolved in the sulfonation product. Saponification of the ester is not observed here. Suitable as neutralization bases include, for example, sodium hydroxide, ammonium hydroxide, diethanolamine, triethanolamine and/or pyridine. Preferably, sodium hydroxide and/or ammonium hydroxide is used. The concentration of the hydroxide and/or amine in water is preferably selected such that the end product forms an aqueous solution which can still flow or is pumpable.

The mixtures of saturated sulfophoshoric acid-(partial)-alkyl esters that are obtained in the process according to the invention contain compounds of general formula II

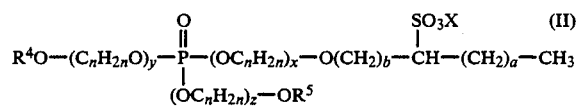

in which $R^4$ and $R^5$ are the same or different and represent hydrogen, or

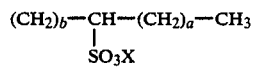

X represents hydrogen, an alkali metal ion, alkaline earth metal ion, ammonium ion or an amine radical, n represents a number from 2 to 4, the subscripts x, y and z are the same or different and represent a number from 0 to 30, and a and b represent a number from 0 to 20 with the proviso that the sum of a+b is between 6 and 20.

Accordingly, the invention also relates to mixtures of surface-active saturated sulfo-phosphoric acid-(partial)-alkyl esters of general formula II.

The surface-active saturated sulfophosphoric acid-(partial)-alkyl esters that are obtained following the process according to the invention are formed as dark to light yellow alkaline solutions in the form of their alkali metal, alkaline earth, ammonium and/or amine salts. If desired, they can be bleached with hydrogen peroxide solutions or alkali metal hypochlorite solutions (sodium hypochlorite) at 40° to 55° C. in a manner known in the art. The pH value of these solutions can be adjusted to neutral using mineral and/or carboxylic acids, e.g. hydrochlorid acid, sulfuric acid, phosphoric acid, citric acid, lactic acid, or mixtures thereof.

The saturated alkyl, saturated alkyl/saturated alkyl polyoxyalkyl and/or saturated alkyl polyoxy alkyl phosphoric acid esters of general formula I which are used as educts, can be obtained according to processes known in the literature. Their manufacture commences with substantially saturated alcohols having an iodine number of between 0 to less than 10. Alcohols with 8 to 22 carbon atoms are preferred, e.g. octyl, decyl, lauryl, myristyl, cetyl, stearyl, and/or behenyl alcohol or industrial alcohol cuts consisting predominatly of these alcohols. In industrial alcohol cuts, small fractions of unsaturated alcohols, e.g. of palmitoleyl and/or oleyl alcohol, are tolerable, particularly when the products manufactured therefrom by oxalkylation are water-soluble. Particularly preferred are alcohols with 12 to 18 carbon atoms or industrial alcohol cuts consisting primarily of lauryl, myristyl, cetyl, and/or stearyl alcohol.

The oxalkylations of the saturated alcohols with ethylene oxide, propylene oxide and/or butylene oxide may be carried out according to known industrial processes (see, for example, in "Chemische Technologie", Vol. 7, page 131–132, Carl-Hanser-Verlag, Munchen-Wien (1986)). The average degree of alkyoxylation represented by x, y or z of the mixtures of homologous alkoxylates obtained corresponds to the molar quantity of the combined alkylene oxides. The saturated sulfophosphoric acid-(partial)-alkyl esters according to the invention of general formula II preferably have degrees of alkoxylation of between 0 and 10.

The phosphating of the saturated, optionally alkoxylated alcohols may be carried out according to known method such as disclosed in Chemische Technologie Vol. 7, page 123 ff, Carl-Hanser-Verlag, Munchen-Wien (1986)). For example, the saturated alcohols and/or saturated alcohol polyoxy alkyl ethers may be reacted with phosphorus pentoxide or polyphosphoric acid. In this process, mixtures of mono-, di- and trialkyl derivatives are formed. When water entrainment agents are used, these partial ester mixtures may also be obtained directly using orthophosphoric acid. At reaction conditions above 160° C. however, no classical esterification takes place. Instead, di- and polyphosphoric acid are primarily formed which react in a known manner with alcohols and/or alcohol polyoxyalkyl ethers. Such extreme reaction conditions also result in the increased formation of olefins.

To manufacture high-purity mono-, di- and trialkylphosphoric acid esters, saturated alcohols and/or saturated alcohol polyoxyalkyl ethers may be reacted with phosphorus oxychloride. This method is less preferred because of the high corrosion risk when phosphorus oxychloride is used.

The saturated sulfophosphoric acid-(partial)-alkyl esters of general formula II according to the invention have a high surface activity and good surfactant properties for industrial application. They have a high foam stability even in hard water and have proved to have good solubility in water despite their high molecular weight. Their marked stability in highly alkaline media, their emulsifying properties and good textile wetting ability are particularly significant.

The following examples are illustrative of the invention.

EXAMPLE 1

Manufacture of saturated alkylphosphate 1.1 Manufacture of $C_{12/14}$-coconut alcohol phosphate 291 g (1.5 mol.) of $C_{12/14}$-coconut oil alcohol (Lorol ® spezial from Henkel KGaA: iodine number of less than 0.3; OH number=290) was placed in a 1 liter three-neck flask provided with a stirrer and thermometer and heated. At a temperature of 60° to 70° C., 71 g (0.5 mol.) of phosphorus pentoxide was introduced gradually over 2 hours using a powder-dosing apparatus protected against air moisture. After a post-reaction period of 2 hours at 70° C., 10 ml of water was added and stirred for a further 3 hours at 90° C.

370 g of a colourless oil was obtained which had the following characteristics:

| | |
|---|---|
| monoalkyl phosphoric acid ester (monoester) | 48.4% by weight |
| dialkyl phosphoric acid ester (diester) | 36.2% by weight |
| trialkyl phosphoric acid ester (triester) | 1.9% by weight |
| $H_3PO_4$ | 0.9% by weight |
| free alcohol | 12.4% by weight |
| $H_2O$ (by Fischer method) | 0.2% by weight |
| iodine number | <0.3 |
| average molecular weight | 343 |
| ester equivalent/mol. | 1.26 |

1.2 Manufacture of $C_{12/18}$-coconut alcohol phosphate

As in Example 1.1, 311 g (1.5 mol.) of $C_{12-18}$-coconut oil alcohol (Lorol® Technisch from Henkel KGaA: iodine number of less than OH number=270) was reacted to $C_{12-18}$-coconut alcohol phosphate. 400 g of a light-coloured oil with the following characteristics was obtained:

| | |
|---|---|
| monoester | 43.8% by weight |
| diester | 44.0% by weight |
| triester | 1.8% by weight |
| $H_3PO_4$ | 0.6% by weight |
| free alcohol | 9.8% by weight |
| $H_2O$ (by Fischer method) | 0.1% by weight |
| iodine number | <0.5 |
| average molecular weight | 374 |
| ester equivalents/mol. | 1.36 |

EXAMPLE 2

Sulfonation of alkylphosphates

2.1 Sulfonation with 30 % excess $SO_3$ 172 g (0.5 mol.) of C12/14-coconut oil alcohol phosphate from example 1.1 was placed in a 1 liter sulfonation reactor with a gas inlet tube and jacket-cooling and reacted at 85° C. with 66 g (0.82 mol.) of $SO_3$ corresponding to a 30% excess based on the ester-equivalents. The $SO_3$ was separated by heating from a corresponding quantity of oleum diluted with nitrogen to a concentration of 5 vol. percent and introduced over 35 minutes into the phosphoric acid alkylester, such that the temperature of the reaction mixture was maintained by cooling to temperatures below 90° C. After the sulfonation, the reaction mixture was aged for 10 minutes at 85° C. under agitation and then stirred into a solution of 40 g (1 mol.) of NaOH in 700 ml of water. After cooling to 20° C., the pH value of the reaction mixture was adjusted to 7.0 by the addition of HCl solution.

Characteristics of the product:

| | |
|---|---|
| anionic surfactant (two-phase titration method according to standard method DGF-H-III-10) | 8% by weight = 0.20 mval/g |
| unsulfonated fractions (DGF-G-III-6b) | 5% by weight |
| sodium sulphate | 3% by weight |
| sodium phosphate | <0.1% by weight |
| $H_2O$ (by Fischer method) | 84% by weight |
| average molecular weight | 403 |
| Klett color number | 154 |

The Klett color number was determined after 30 minutes of bleaching with 5% by weight of a 35% hydrogen peroxide solution. The measurement was carried out at a concentration of 5% by weight of anionic surfacant, pH 7 and using a 1-cm cuvette and a blue filter (400–465 μ).

2.2 Sulfonation with 60% excess $SO_3$

As in Example 2.1, 80 g (1.00 1 mol.) of $SO_3$ corresponding to a 60% $SO_3$ excess based on the ester equivalents was introduced over 41 minutes into 172 g (0.5 mol.) of $C_{12/14}$-coconut oil alcohol phosphate from example 1.1. The neutralization was carried out with 48 g (1.2 mol.) NaOH in 800 ml of water.

The product obtained had the following characteristics:

| | |
|---|---|
| anionic surfactant (DGF-H-III-10) | 11% by weight = 0.27 mval/g |
| unsulfonated fractions (DGF-G-III-6b) | 8% by weight |
| $Na_2SO_4$ | 5% by weight |
| $Na_3PO_4$ | <0.1% by weight |
| $H_2O$ (by Fischer method) | 76% by weight |
| average molecular weight | 413 |
| Klett color number | 298 |

2.3 Sulfonation at 100° C.

The process described in Example 2.1 was repeated at a sulfonation temperature of 100° C. The product obtained had the following characteristics:

| | |
|---|---|
| anionic surfactant (DGF-H-III-10) | 15% by weight = 0.36 mval/g |
| unsulfonated fractions (DGF-G-III-6b) | 10% by weight |
| $Na_2SO_4$ | 1% by weight |
| $Na_3PO_4$ | <0.1% by weight |
| $H_2O$ (by Fischer method) | 74% by weight |
| average molecular weight | 418 |
| Klett color number | 559 |

2.4 Variation of the aging temperature

The process described in Example 2.1 was repeated, except that aging of the product was carried out in 10 minute at 100° C. The product obtained had the following characteristics:

| | |
|---|---|
| anionic surfactant (DGF-H-III-10) | 9% by weight = 0.41 mval/g |
| unsulfonated fractions (DGF-G-III-6b) | 5% by weight |
| Na2SO4 | 3% by weight |
| Na3PO4 | <0.1% by weight |
| H2O (by Fischer method) | 81 |
| average molecular weight | 413 |
| Klett color number | 214 |

2.5 Variation of the aging period

The process described in Example 2.2 was repeated, except that aging of the product was carried out in 30 minutes at 85° C. The product obtained has the following characteristics:

| | |
|---|---|
| anionic surfactant (DGF-H-III-10) | 8% by weight = 0.41 mval/g |
| unsulfonated fractions (DGF-G-III-6b) | 5% by weight |
| Na2SO4 | 4% by weight |
| NA3PO4 | <0.1% by weight |
| H2O (by Fischer method) | 83% by weight |
| average molecular weight | 413 |
| Klett color number | 322 |

2.6 Sulfonation of $C_{12-18}$-coconut oil alcohol phosphate

As in Example 2.1, 103 g (0.5 mol.) of $C_{12-18}$-coconut oil alcohol phosphate from example 1.2 was reacted with 72 g (0.88 mol.) of $SO_3$ corresponding to a 30% excess based on the ester-equivalents. The product obtained had the following characteristics:

| | |
|---|---|
| anionic surfactant (DGF-H-III-10) | 8% by weight = 0.18 mval/g |
| unsulfonated fractions (DGF-G-III-6b) | 5% by weight |
| Na2SO4 | 3% by weight |
| Na3PO4 | <0.1% by weight |
| H2O (by Fischer method) | 82% by weight |
| average molecular weight | 438 |
| Klett color number | 186 |

2.7 Neutralization with ammonium hydroxide

The process described in Example 2.1 was repeated, except that the neutralization was carried out with 68 g (1 mol.) of concentrated (25%) ammonium hydroxide solution in 200 ml of water in a sealed apparatus under reflux. The product obtained had the following characteristics:

| | |
|---|---|
| anionic surfactant (DGF-H-III-10) | 46% by weight = 1.10 mval/g |
| unsulfonated fractions (DGF-G-III-6b) | 18% by weight |
| Na2SO4 | 8% by weight |
| Na3PO4 | <0.1% by weight |
| H2O (by Fischer method) | 28% by weight |
| average molecular weight | 438 |
| Klett color number | 76 |

2.8 Sulfonation in the fall film reactor

In a continuously operating fall-film reactor, 1.8 kg (5.20 mol.) of $C_{12/14}$-coconut oil alcohol phosphate from Example 1.1 at a through-put of 10 g/min. was reacted with $SO_3$ in the molar ratio ester equivalents: $SO_3 = 1:1.3$. The sulfonation product obtained was then aged continuously at 85° C. for 10 minute and then stirred into concentrated sodium hydroxide solution (45%) and adjusted as described in 2.1. The product obtained had the following characteristics:

| | |
|---|---|
| anionic surfactant (DGF-H-III-10) | 40% by weight = 0.96 mval/g |
| unsulfonated fractions (DGF-G-III-6b) | 8% by weight |
| Na2SO4 | 2% by weight |
| Na3PO4 | <0.1% by weight |
| H2O (by Fischer method) | 50% by weight |
| average molecular weight | 418 |
| Klett color number | 124 |

We claim:

1. A process for producing an aqueous solution of surface-active, saturated sulfophosphoric acid-(partial)-alkyl esters and their alkali metal, alkaline earth, ammonium and amine salts thereof comprising:

(a) providing saturated alkyl, saturated alkyl/-saturated alkylpolyoxyalkyl, and/or saturated alkylpolyoxyalkylphosphates with iodine numbers between 0 and less than 10, which correspond to general formula I

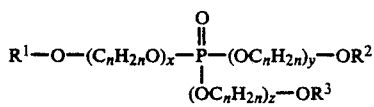
(I)

wherein $R^1$ represents an alkyl groups with 8 to 22 carbon atoms or a fatty alkyl group consisting predominantly of octyl, decyl, lauryl, myristyl, cetyl, stearyl or behenyl groups, the radicals $R^2$ and $R^3$ are the same or different and represent hydrogen, an alkyl group with 8 to 22 carbon atoms or a fatty alkyl group consisting predominantly of octyl, decyl, lauryl, myristyl, cetyl, stearyl or behenyl groups, n is a number from 2 to 4, the subscripts x, y and z are the same or different and represent a number between 0 and 30;

(b) sulfonating the product of step (a) at a temperature of between about 60° C. and about 100° C.; and (c) hydrolyzing the sulfonation product of step (b) with a base.

2. A process in accordance with claim 1 wherein said hydrolyzing step (c) is performed by reacting the sulfonation product of step (b) with from about 1 to about 1.5 mole of alkali metal hydroxide, alkaline earth hydroxide, ammonium hydroxide or amine per mole of sulfonating agent.

3. A process in accordance with claim 1 wherein said sulfonating step (b) is performed by reacting the product of step (a) with a sulfonation agent selected from the group consisting of sulfuric acid, chlorosulfonic acid, oleum, and gaseous mixtures containing $SO_3$.

4. A process in accordance with claim 1 wherein $R^1$ represents an alkyl group with 12 to 18 carbon atoms or a fatty alkyl group consisting predominatly of lauryl, myristyl, cetyl or stearyl groups, the radicals $R^2$ and $R^3$ are the same or different and represent hydrogen, an alkyl group with 12 to 18 carbon atoms or a fatty alkyl group consisting predominatly of lauryl, myristyl, cetyl or stearyl groups, n is a number from 2 to 3, and the subscripts x, y and z are the same or different and represent a number between 0 and 10.

5. A process in accordance with claim 1 wherein said sulfonating step (b) is carried out with a gaseous mixture of gaseous $SO_3$ and air or inert gas wherein the $SO_3$ content thereof is between about 1 and about 10 percent by volume.

6. A process in accordance with claim 5 wherein the molar ratio of the ester equivalents contained in the educt to $SO_3$ is between about 100:5 and about 100:180.

7. A process in accordance with claim 6 wherein said molar ratio is between about 100:10 and about 100:160.

8. A process in accordance with claim 1 wherein after said sulfonating step (b) and prior to said hydrolyzing step (c), the step of aging the sulfonated reaction products for up to about 240 minutes at a temperature of between about 10 and about 120° C.

9. A process in accordance with claim 8 wherein said aging is conducted for between about 1 and about 30 minutes at a temperature of between about 60 and about 100° C.

10. A process in accordance with claim 1 wherein said base is selected from the group consisting of sodium hydroxide, ammonium hydroxide, diethanolamine, triethanolamine and pyridine.

11. An aqueous solution of a mixture of surface-active, saturated sulfophsophoric acid-(partial)-alkyl esters of general formula II

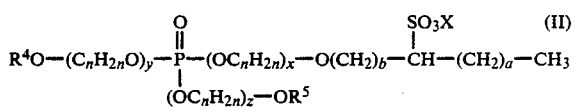
(II)

in which $R^4$ and $R^5$ are the same or different and represent hydrogen or

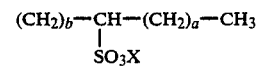

X represents hydrogen, an alkali metal ion, alkaline earth metal ion, ammonium ion or an amine radical, n represents a number from 2 to 4, the subscripts x, y and z are the same or different and represent a number from 0 to 30, a represents a number from 0 to 20 and b represents a number from 0 to 20 with the proviso that the sum for a+b is between about 6 and about 20, prepared by the process of claim 1.

* * * * *